(12) United States Patent
Kalman

(10) Patent No.: US 10,751,358 B2
(45) Date of Patent: Aug. 25, 2020

(54) MULTITARGETED NUCLEOSIDE DERIVATIVES

(71) Applicant: Thomas I. Kalman, East Amherst, NY (US)

(72) Inventor: Thomas I. Kalman, East Amherst, NY (US)

( * ) Notice: Subject to any disclaimer, the term of this patent is extended or adjusted under 35 U.S.C. 154(b) by 0 days.

(21) Appl. No.: 16/664,522

(22) Filed: Oct. 25, 2019

(65) Prior Publication Data
US 2020/0054661 A1 Feb. 20, 2020

Related U.S. Application Data

(63) Continuation-in-part of application No. PCT/US2018/029631, filed on Apr. 26, 2018.

(60) Provisional application No. 62/490,212, filed on Apr. 26, 2017.

(51) Int. Cl.
| | |
|---|---|
| A61K 31/7068 | (2006.01) |
| A61K 33/243 | (2019.01) |
| A61K 31/337 | (2006.01) |
| A61K 31/4745 | (2006.01) |
| A61K 31/519 | (2006.01) |
| C07H 17/02 | (2006.01) |
| C07H 19/06 | (2006.01) |
| C07H 19/10 | (2006.01) |
| A61K 31/7076 | (2006.01) |

(52) U.S. Cl.
CPC ........ *A61K 31/7068* (2013.01); *A61K 31/337* (2013.01); *A61K 31/4745* (2013.01); *A61K 31/519* (2013.01); *A61K 31/7076* (2013.01); *A61K 33/243* (2019.01); *C07H 17/02* (2013.01); *C07H 19/06* (2013.01); *C07H 19/10* (2013.01)

(58) Field of Classification Search
CPC ........ C07H 19/10; C07H 19/06; C07H 17/02; A61K 31/7068; A61K 31/7076; A61K 31/519; A61K 31/4745; A61K 31/337; A61K 33/243

See application file for complete search history.

(56) References Cited

U.S. PATENT DOCUMENTS

| | | | |
|---|---|---|---|
| 4,692,434 A | 9/1987 | Hertel | |
| 4,966,891 A | 10/1990 | Fujiu et al. | |
| 8,603,998 B2 | 12/2013 | Guzi et al. | |
| 2004/0002476 A1 | 1/2004 | Stuyver et al. | |
| 2008/0145372 A1* | 6/2008 | Davis | C07H 19/16 424/178.1 |
| 2011/0269689 A1 | 11/2011 | Yu et al. | |
| 2017/0233428 A1* | 8/2017 | Coats | A61K 45/06 424/85.4 |

FOREIGN PATENT DOCUMENTS

| | | |
|---|---|---|
| EP | 0376518 A1 | 7/1990 |
| EP | 0577303 A1 | 1/1994 |
| WO | 2006092808 A1 | 9/2006 |
| WO | 2014078295 A1 | 5/2014 |

OTHER PUBLICATIONS

Shimma, N. et al., The Design and Synthesis of a New Tumor-Selective Fluoropyrimidine Carbamate, Capecitabine, Bioorganic & Medicinal Chemistry, 2000, vol. 8, pp. 1697-1706.

Slusarczyk, M. et al., Application of ProTide Technology to Gemcitabine: A Successful Approach to Overcome the Key Cancer Resistance Mechanisms Leads to a New Agent (NUC-1031) in Clinical Development, Journal of Medicinal Chemistry, Jan. 28, 2014, vol. 57, pp. 1531-1542.

Kotra, L.P., et al., Structure-Activity Relationships of 2'-Deoxy-2',2'-difluoro-L-erythro-pentofuranosyl Nucleosides, J. Med. Chem., 1997, vol. 40, pp. 3635-3644.

* cited by examiner

*Primary Examiner* — Jonathan S Lau
(74) *Attorney, Agent, or Firm* — Hodgson Russ LLP

(57) ABSTRACT

Multitargeted pyrimidine nucleoside carbamates, substituted with fluorine at both the base and the sugar moieties, are disclosed (see Formula I):

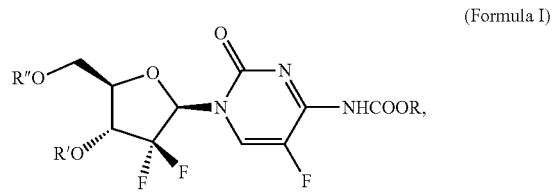

(Formula I)

where R=linear or branched alkyl ($C_{1-7}$); R'=H, hydroxy protecting group; R"=H, phosphate ester, amino acid alkyl ($C_{1-7}$) ester phoshoramidate, or phosphorodiamidate. The disclosed compounds are fluoropyrimidine prodrugs that are characterized by a novel combination of structural components that provide intracellular metabolites capable of 1) inhibiting several cellular enzymes required for the synthesis and proper functioning of DNA, and 2) causing DNA damage by misincorporation into DNA. By acting on multiple targets with different mechanisms of action, compounds of Formula I reduce the likelihood of the emergence of drug resistance, a major drawback of the use of nucleoside-based anticancer and antiviral drugs. Due to the metabolic activation profile of compounds of Formula I, characteristic adverse effects and potential lethality of the fluoropyrimidine class of anticancer drugs may be alleviated. Compounds and compositions of the present disclosure can be used in treatment of cancer and viral infections.

21 Claims, 2 Drawing Sheets

MULTITARGETED NUCLEOSIDE DERIVATIVES

CROSS REFERENCE TO RELATED APPLICATIONS

This application is a continuation-in-part of International Application No. PCT/US2018/029631, filed on Apr. 26, 2018, which claims priority to U.S. Provisional Application No. 62/490,212, filed on Apr. 26, 2017, the disclosures of which are incorporated herein by reference.

FIELD OF THE DISCLOSURE

The disclosure generally relates to nucleoside derivatives. More particularly, the disclosure relates to fluoropyrimidines for treatment of cancer and viral infections.

BACKGROUND OF THE DISCLOSURE

As of 2013, 36 nucleoside or nucleotide analogs approved by the FDA were available for medicinal use; of these, 11 are anticancer agents and 25 are antiviral drugs (Jordheim, L. P. et al., "Advances in the Development of Nucleoside and Nucleotide Analogues for Cancer and Viral Diseases," *Nature Reviews: Drug Discovery*, 2013, 12, 447-464). The therapeutic utility of these analogs stems from their ability to interfere with the replication and function of cellular or viral nucleic acids. Their mechanisms of action involve inhibition of enzymes required for the synthesis and replication of cellular or viral nucleic acids, and/or their ability to be incorporated into nucleic acids.

Cancer and viruses are characterized by their ability to develop resistance to the drugs used against them in conventional therapies. This is particularly prevalent with analogs of nucleic acid components, such as nucleobase, nucleoside and nucleotide analogs, which act as antimetabolites. The practice of using a combination of different drugs was evolved to fight drug resistance, however, even combination chemotherapy could not eliminate the drug resistance problem, since cross resistance may also develop against multiple drugs. The increasing prevalence of these drug resistant cancers and viruses necessitates the continued discovery and development of new, more effective therapeutic agents.

5-Fluorouracil (FU), the prototype of the anticancer fluoropyrimidines, is an antimetabolite discovered in 1957 that is still in use alone or in combination with other anticancer agents, or with biological response modifiers, particularly in the treatment of colorectal and breast cancer. Major shortcomings of FU include inadequate oral bioavailabilty, severe toxic side effects, and pharmacogenetic liability in patients with a deficiency of FU degrading enzymes, which can be lethal. Over the past six decades, numerous prodrug derivatives of FU, as well as several nucleoside analogs and drug combinations have been developed to overcome toxic side effects, increase the therapeutic effectiveness and the therapeutic index. However, what remains is an unmet need of developing new, orally available anticancer fluoropyrimidines that are devoid of the major side effects, such as gastro-intestinal and bone marrow toxicity, hand and foot syndrome and pharmacogenetic syndrome (dihydropyrimidine dehydrogenase deficiency (DPD deficiency)), among others.

The fluoropyrimidine capecitabine (Xeloda®) is the sole nucleoside carbamate approved by the FDA and the most advanced fluoropyrimidine so far developed. It is a prodrug of 5-fluorouracil (FU). While sharing some of the shortcomings of FU, capecitabine is available orally, causes less GI toxicity characteristic of fluoropyrimidines by becoming activated primarily in the liver, and not during intestinal absorption. These advances have been attributed to the carbamate side chain at the $N^4$-position of the 5-fluorocytosine moiety of this nucleoside analog. However, hand and foot syndrome is often the dose limiting toxicity of capecitabine leading to significant morbidity. Thymidine phosphorylase, the enzyme responsible for the obligatory conversion of capecitabine to the cytotoxic FU, has significant activity in some normal tissues, such as the palm, and may play a role in the etiology of hand and foot syndrome. Furthermore, inherited DPD deficiency, which can put patients at risk of severe or lethal toxicities, is also linked to FU that is an obligatory intermediate in the metabolic activation of capecitabine by thymidine phosphorylase.

There exists an ongoing and unmet need for nucleosides with less harmful side effects.

SUMMARY OF THE DISCLOSURE

The present disclosure provides novel, multitargeted pyrimidine nucleoside carbamates, substituted with fluorine at both the base and the sugar moieties (see Formula I):

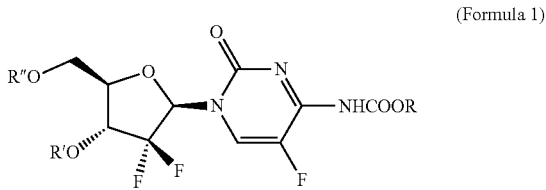

(Formula 1)

where R is a linear or branched alkyl group ($C_{1-7}$); R' is H, or a hydroxy protecting group (e.g., an amino acyl group or acyl group, such as, for example, acetyl or benzoyl); R" is H, a phosphate ester, an amino acid alkyl ($C_{1-7}$) ester phoshoramidate, or a phosphorodiamidate.

The disclosed compounds are prodrugs that are characterized by a novel combination of structural components that provide intracellular metabolites capable of inhibiting several cellular enzymes required for the synthesis and proper functioning of DNA. In addition, the disclosed compounds can cause DNA damage by analog misincorporation into DNA. Such DNA damage may lead to the death of a cancer cell by apoptosis.

By acting on multiple targets with different mechanisms of action, compounds of Formula I reduce the likelihood of the emergence of drug resistance, a major drawback of the use of nucleoside-based anticancer and antiviral drugs. Thus, each of the disclosed compounds can achieve the effects of combination chemotherapy via administration of a single compound with a single pharmacokinetic profile. A desirable characteristic of the disclosed compounds is that unlike all other fluoropyrimidines, they cannot be converted to the highly toxic FU by metabolism, therefore they are devoid of most of the undesirable effects of FU.

The present disclosure provides methods of making the compounds of Formula I. The methods are based on a specific amount of TMSOTf employed as the Lewis acid in the glycosylation reaction.

In an example, a method of making a compound of the present disclosure comprises: providing a reaction mixture comprising 5-fluoro-N-(trimethylsilyl)-2-((trimethylsilyl)oxy)pyrimidin-4-amine

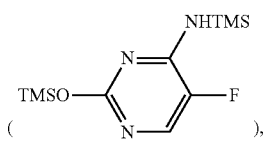

( ), (2R,4R,5R)-4-(benzyloxy)-5-((benzyloxy)methyl)-3,3-difluorotetrahydrofuran-2-yl methanesulfonate

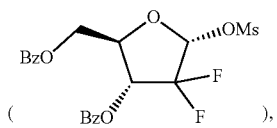

( ), and a solvent (e.g., dichloroethane), adding to the reaction mixture 3 equivalents of TMSOTf to yield the ca/β anomeric mixture of (2R,3R)-5-(4-amino-5-fluoro-2-oxopyrimidin-1(2H)-yl)-2-((benzoyloxy)methyl)-4,4-difluorotetrahydrofuran-3-yl benzoate

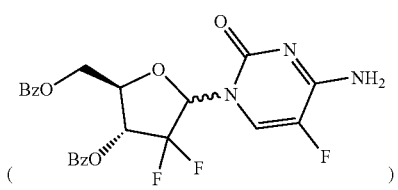

( )

in 100% yield. The product can be used to produce a compound of the present disclosure using methods disclosed herein.

The present disclosure provides compositions comprising one or more compound of Formula I, and pharmaceutically acceptable salts thereof. The compositions can comprise one or more pharmaceutically acceptable carrier.

The design principles that lead to the compounds of the present disclosure can be summarized as follows. It is generally accepted that the activation by thymidine phosphorylase (TP) of capecitabine, an advanced prior fluoropyrimidine, is an advantage because some cancers overexpress this enzyme. Contrary to the prevailing views, it was hypothesized in the present disclosure that designing away the substrate activity for TP may be more advantageous, because that would prevent formation of FU and its associated toxic side effects, having favorable impact on all patients, not just those with cancers of high TP expression. It was considered that placing a fluorine, the most electronegative atom, at the 2'-position of the analog would destabilize the transition state of the TP reaction that has a positive charge density at the adjacent 1'-carbon (see Schwartz, P. A. et al., *Journal of the American Chemical Society* 2010, 132, 14425). It was further considered that adding another fluorine would result in a greater effect. However, it was recognized that eliminating the involvement of TP would prevent the sole metabolic activation of the analog, therefore it was necessary to add an —OH group at the 5'-position that would permit an alternative pathway of activation by kinase-mediated phosphorylation (see FIG. 2).

The present disclosure provides methods of using one or more compounds of the present disclosure. For example, the compounds can be used to treat cancer and/or viral infections.

BRIEF DESCRIPTION OF THE FIGURES

For a fuller understanding of the nature and objects of the disclosure, reference should be made to the following detailed description taken in conjunction with the accompanying figures.

DETAILED DESCRIPTION OF THE DISCLOSURE

Figure 1:
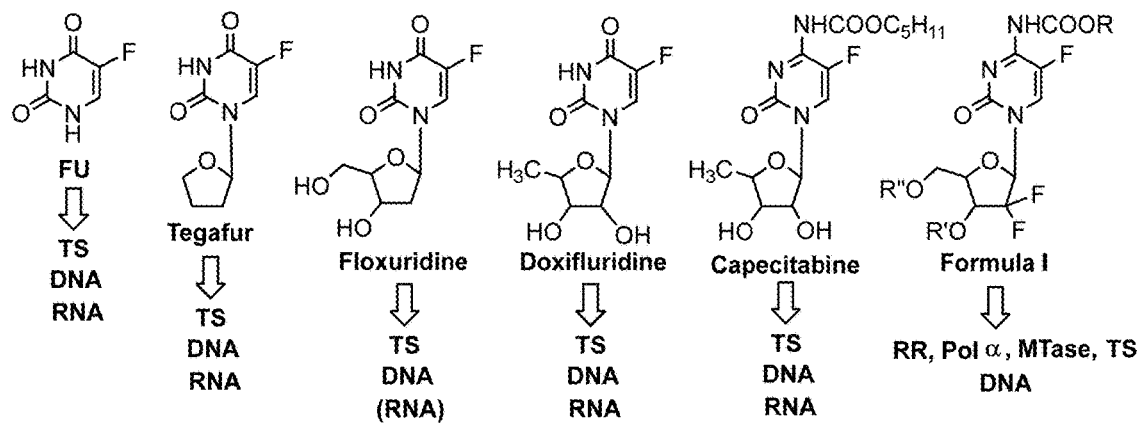
FIG. 1 shows the major targets of the fluoropyrimidines in clinical use in comparison with those of Formula I.

Although claimed subject matter will be described in terms of certain embodiments, other embodiments, including embodiments that do not provide all of the benefits and features set forth herein, are also within the scope of this disclosure. Various structural, logical, and process step changes may be made without departing from the scope of the disclosure.

The present disclosure provides novel, multitargeted pyrimidine nucleoside carbamates, substituted with fluorine at both the base and the sugar moieties (see Formula I):

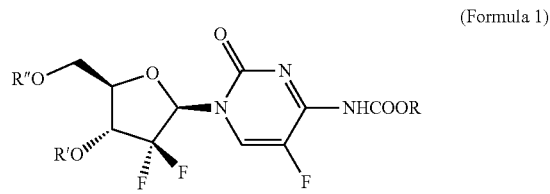

(Formula 1)

where R is a linear or branched alkyl group ($C_{1-7}$); R' is H, hydroxy protecting group; R" is H, a phosphate ester, an amino acid alkyl ($C_{1-7}$) ester phosphoramidate, or a phosphorodiamidate; or a pharmaceutically acceptable salt thereof. In an example, the R" can be a monophosphate, diphosphate, triphosphate, or phosphoramidate.

Examples of hydroxy protecting groups are known in the art. For example, hydroxy protecting groups can include amino acyl and acyl groups. Non-limiting examples of acyl groups include acetyl groups and benzoyl groups.

In various examples, the pyrimidine nucleoside carbamates have the following structure:

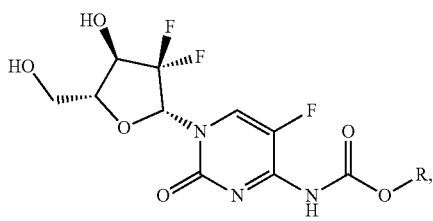

where R is a linear or branched alkyl group ($C_{1-7}$), or a pharmaceutically acceptable salt thereof.

The disclosed compounds are prodrugs that are characterized by a novel combination of structural components that provide intracellular metabolites capable of inhibiting several cellular enzymes required for the synthesis and proper functioning of DNA, and of causing DNA damage by misincorporation into DNA. By acting on multiple targets with different mechanisms of action, compounds of Formula I reduce the likelihood of the emergence of drug resistance, a major drawback of the use of nucleoside-based anticancer and antiviral drugs. Thus, each of the disclosed compounds can achieve the effects of combination chemotherapy via administration of a single compound with a single pharmacokinetic profile. In a drug combination, due to the different structures of the combined drugs, it is difficult to optimize the differences between individual ADME properties for maximum benefit. A desirable characteristic of the disclosed compounds is that unlike all other fluoropyrimidines, they cannot be converted to the highly toxic FU by metabolism, therefore they are devoid of most of the undesirable effects of FU.

The compounds disclosed herein undergo a different prodrug activation pathway than capectabine. This pathway does not involve thymidine phosphorylase and does not produce FU (see FIG. 2). Therefore, in contrast to other fluoropyrimidines in clinical use, compounds of Formula I are expected to lack the potentially lethal toxic side effects in people caused by FU.

One of the metabolites of the Formula I compounds, $F_3dUrd$ (see FIG. 2), could theoretically be cleaved by thymidine phosphorylase to produce FU. However, when tested, it was found that $F_3dUrd$ did not serve as a substrate for thymidine phosphorylase, confirming the original hypothesis that formed the basis of the design of the Formula I compounds. Floxuridine (FdUrd), which lacks the two fluorine atoms at the 2'-position, was found to be rapidly cleaved by thymidine phosphorylase to produce FU, as expected.

The fundamental structural differences between capecitabine and a representative member of the Formula I compounds 6a that most closely resembles capecitabine having an identical carbamate side chain, are highlighted below:

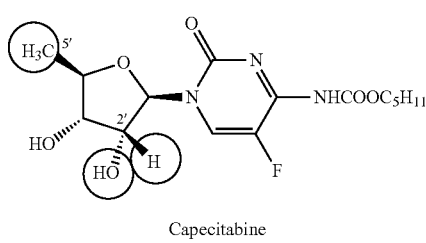

Capecitabine

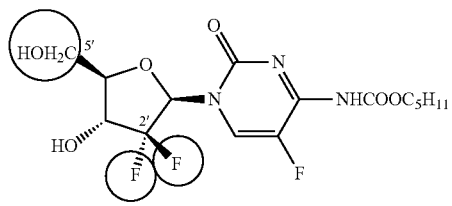

$R = C_5H_{11}, R' = R'' = H$ (6a)

At the 5'-position of capecitabine there is a methyl group. In contrast, 6a has a hydroxymethyl group at the 5'-position that unlike the methyl group in capecitabine, permits intracellular phosphorylation of the free nucleoside $F_3dCyd$ to its monophosphate, after hydrolysis of the carbamate side chain and cellular uptake (see FIG. 2).

At the 2'-position, there are 2 differences. Both the 2'-hydroxy group and the 2'-hydrogen of capecitabine are missing in Formula I. Instead, there are two fluorine atoms at the 2'-position of 6a. These fluorine atoms stabilize the glycosyl bond against cleavage and provide the chemistry for inactivation of the essential enzyme ribonucleotide reductase. In contrast, glycosyl bond cleavage is an obligatory step in the metabolic activation of capecitabine, forming FU, and ribonucleotide reductase activity is not affected.

The design principles that lead to the compounds of the present disclosure can be summarized as follows. It is generally accepted that the activation by thymidine phosphorylase (TP) of capecitabine, an advanced prior fluoropyrimidine, is an improvement because some cancers overexpress this enzyme. It was hypothesized that contrary to the prevailing views, designing away the substrate activity for TP may be more advantageous, because that would prevent formation of FU that is responsible for most of the toxic side effects, having favorable impact on all patients, not just those with cancers of high TP expression. It was considered that placing a fluorine, the most electronegative atom, at the 2'-position of the analog would destabilize the transition state of the TP reaction that has a positive charge density at the adjacent 1'-carbon (see Schwartz, P. A. et al., *Journal of the American Chemical Society* 2010, 132, 14425). It was further considered that adding another fluorine would result in a greater effect. However, eliminating the involvement of TP would prevent metabolic activation of the analog, an —OH group was added at the 5'-position to permit an alternative pathway of activation by kinase-mediated phosphorylation (see FIG. 2).

The scheme below outlines the important steps in the metabolic activation pathway of capecitabine, leading to the "parent drug," FU:

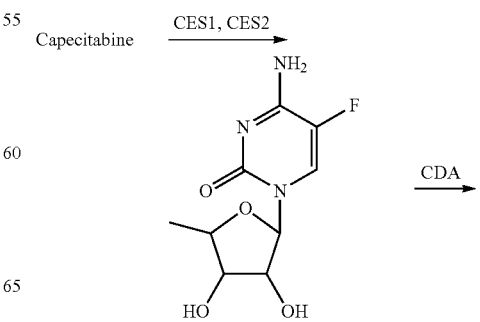

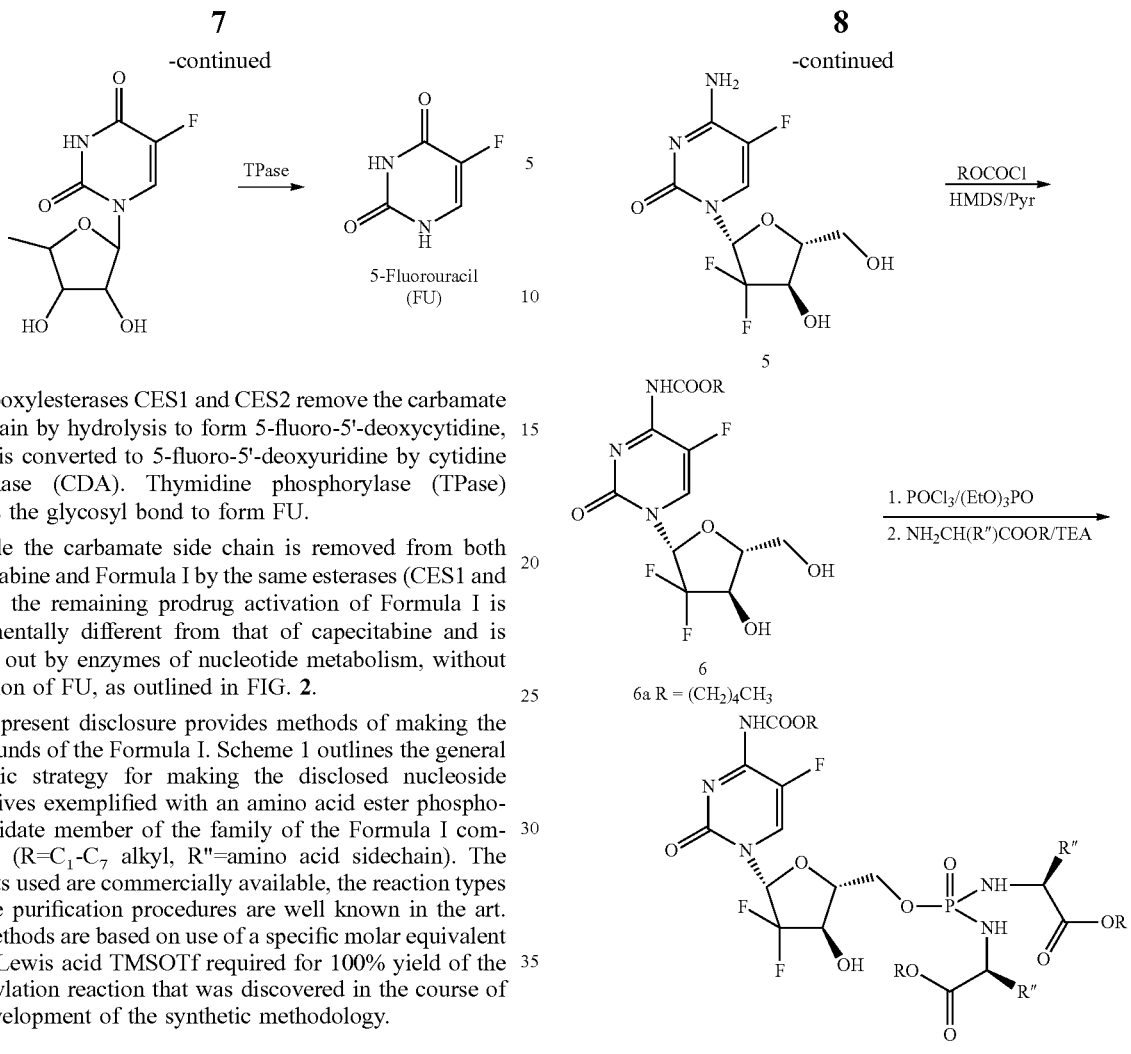

Carboxylesterases CES1 and CES2 remove the carbamate side chain by hydrolysis to form 5-fluoro-5'-deoxycytidine, which is converted to 5-fluoro-5'-deoxyuridine by cytidine deaminase (CDA). Thymidine phosphorylase (TPase) cleaves the glycosyl bond to form FU.

Figure 2:
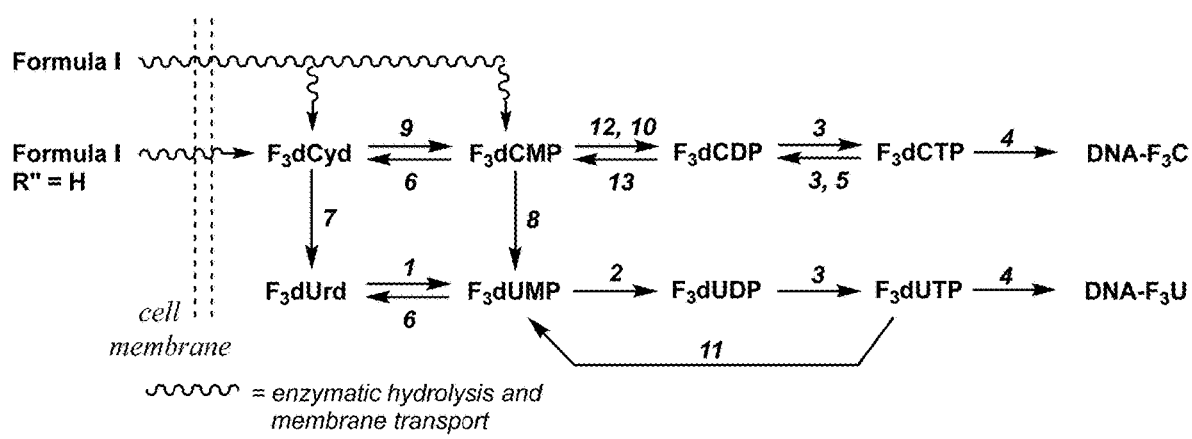
FIG. 2 shows metabolic pathways for a compound of the present disclosure. The numbers in the figure correspond to the following enzymes: (1) thymidine kinase (TK), EC 2.7.1.21; (2) thymidylate kinase (dTMPK), EC 2.7.4.9; (3) nucleoside-diphosphate kinase (NDPK), EC 2.7.4.6; (4) DNA polymerase α (Pol α), EC 2.7.7.7; (5) nucleoside triphosphatase (NTPase), EC 3.6.1.15; (6) 5'-nucleotidase (5'-NT), EC 3.1.3.5; (7) cytidine deaminase (CDA) EC 3.5.4.5; (8) deoxycytidylate (dCMP) deaminase (DCTD), EC 3.5.4.12; (9) deoxycytidine kinase (dCK), EC 2.7.1.74; (10) UMP/CMP kinase (YMPK), EC 2.7.4.14; (11) dUTP diphosphatase (dUTPase), EC 3.6.1.23; (12) dCMP kinase (DCMPK), EC 2.7.4.25; and (13) nucleoside diphosphatase (NDPase), EC 3.6.1.6.

While the carbamate side chain is removed from both capecitabine and Formula I by the same esterases (CES1 and CES2), the remaining prodrug activation of Formula I is fundamentally different from that of capecitabine and is carried out by enzymes of nucleotide metabolism, without formation of FU, as outlined in FIG. 2.

The present disclosure provides methods of making the compounds of the Formula I. Scheme 1 outlines the general synthetic strategy for making the disclosed nucleoside derivatives exemplified with an amino acid ester phosphorodiamidate member of the family of the Formula I compounds (R=$C_1$-$C_7$ alkyl, R"=amino acid sidechain). The reagents used are commercially available, the reaction types and the purification procedures are well known in the art. The methods are based on use of a specific molar equivalent of the Lewis acid TMSOTf required for 100% yield of the glycosylation reaction that was discovered in the course of the development of the synthetic methodology.

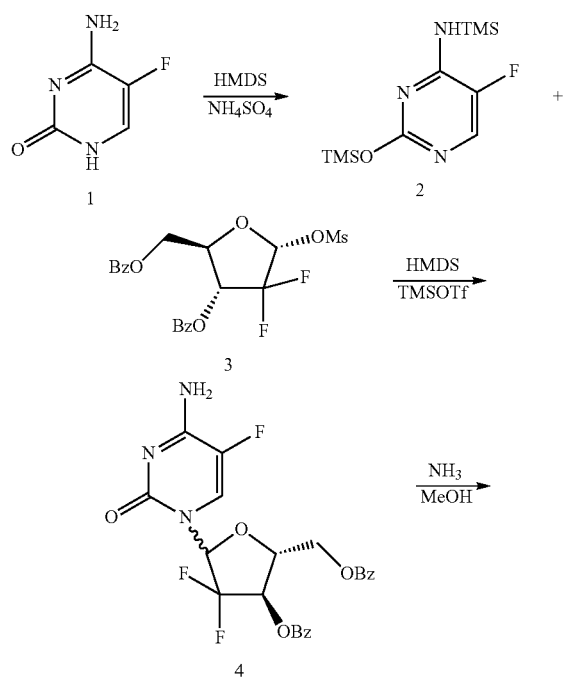

Scheme 1. Synthetic Outline

The yield of coupling of 2 and 3 to form the anomeric mixture of 4 was found to be greatly dependent on the molar excess of trimethylsilyl trifluoromethanesulfonate (TMSOTf). It was discovered that, whereas the yield was only 8% using 1.0 eq of TMSOTf, increasing the TMSOTf to 2.55, 2.75 and 3.0 eq increased the yield to 58, 85 and 100%, respectively.

The synthesis of intermediates 4 and 5 were previously disclosed, however, their preparation involved only a 2-fold excess of TMSOTf, for the condensation reaction and the resolution of the anomeric mixture 4 produced during the glycosylation process required chiral chromatography. Furthermore, the isolation of the pure β-anomer 5 required additional chromatographic purification. The method previously reported was a modification of a literature procedure (Kotra, L P, et al., *J. Med. Chem.* 1997, 40, 3635-3644) for the preparation of the L-enantiomers of 4, which involved a 2-fold excess of TMSOTf for the condensation reaction yielding 57% of the anomeric mixture.

In contrast, the method disclosed herein (see Examples 1 and 2) employed a 3:1 molar excess of TMSOTf with a 100% yield of the anomeric mixture in the condensation reaction, furthermore, the isolation of the pure β-anomer was performed without resorting to any of the customary chromatographic steps used in the art, greatly simplifying the procedure.

In an example, a method of making a compound of the present disclosure comprises: providing a reaction mixture comprising 5-fluoro-N-(trimethylsilyl)-2-((trimethylsilyl)oxy)pyrimidin-4-amine

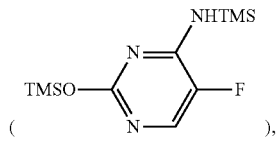

(2R,4R,5R)-4-(benzyloxy)-5-((benzyloxy)methyl)-3,3-difluorotetrahydrofuran-2-yl methanesulfonate

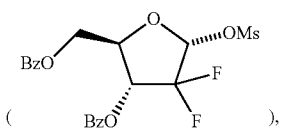

and a solvent (e.g., dichloroethane), adding to the reaction mixture 3 equivalents of TMSOTf to yield the product (2R,3R)-5-(4-amino-5-fluoro-2-oxopyrimidin-1(2H)-yl)-2-((benzoyloxy)methyl)-4,4-difluorotetrahydrofuran-3-yl benzoate

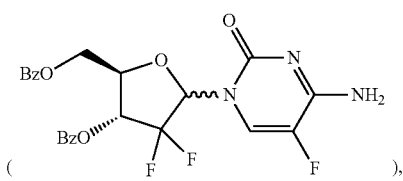

as a 1.2:1.0 mixture of α and β anomers. The pure β anomer of the free nucleoside 5 was obtained as described in Example 2, without the customary chromatographic separation of the anomeric mixture. Compound 5 can be used to produce a compound of the present disclosure using methods disclosed herein.

Compounds of Formula I are fluoropyrimidines that differ from the other fluoropyrimidines, such as FU, tegafur, doxifluriodine, floxuridine and capecitabine on the basis of chemical composition and biological activities. The major targets of the prior fluoropyrimidines have been established and include the following:
  (i) the enzyme thymidylate synthase
  (ii) the nucleic acid DNA by misincorporation of FU and uracil
  (iii) the nucleic acid RNA by misincorporation of FU Misincorporation into RNA is an undesirable effect, because it adversely affects RNA synthesis and function in non-dividing normal cells, as well as the cancer cells, lowering the selectivity index of all existing fluoropyrimidines. In contrast, misincorporation into DNA affects dividing cells only, contributing to the cytotoxicity of fluoropyrimidines, with selectivity toward proliferating cells.

It was discovered that the Formula I compounds also target thymidylate synthase and DNA, but not RNA. Furthermore, Formula I compounds were found to target the following additional enzymes: ribonucleotide reductase, DNA-polymerase c and DNA (cytosine-5) methyltransferase via a variety of intracellular nucleotide analogs produced by their metabolic activation. The major targets of the known fluoropyrimidines, in comparison with Formula I, are illustrated in FIG. 1.

It was also found that compounds of Formula I misincorporated into DNA 5-fluorocytosine, in addition to FU and uracil. Furthermore, the incorporated FU was linked to 2,2-difluoro-2-deoxyribose, instead of the natural 2'-deoxyribose in the case of the other fluoropyrimidines, likely causing additional effects on DNA structure and function.

The various misincorporated nucleotides interfere with DNA replication and/or function, and induce specific DNA repair processes with varying outcomes, depending on the nature and extent of DNA damage they cause. Without intending to be bound by any particular theory, DNA damage can lead to the death by apoptosis of the cancer cell exposed to compounds of Formula I.

The above comparisons reveal that Formula I compounds inhibit more essential enzymes and create DNA damage by misincorporation of more aberrant nucleotides into DNA, than previous anticancer fluoropyrimidines in clinical use. Consequently, the disclosed compounds may decrease the likelihood of the emergence of drug resistance against themselves, and are less prone to cross resistance with the other fluoropyrimidine analogs during their therapeutic applications.

Another unique aspect of the present disclosure is that compounds of Formula I cause incorporation of 5-fluorocytosine into DNA that results in irreversible inactivation of DNA (cytosine-5)-methyltransferase. None of the FDA approved anticancer nucleoside analogs are capable of incorporating 5-fluorocytosine into DNA. Inactivation of DNA (cytosine-5)-methyltransferase results in the elimination of 5-methylcytosine residues in specific CpG sequences in DNA, resulting in "demethylation," interfering with the epigenetic regulation of cellular metabolism.

The capecitabine molecule also contains the 5-fluorocytosine base, however, it becomes converted to the corresponding 5-fluorouracil by deamination during metabolic activation of the drug. Therefore, in contrast to the present disclosure, capecitabine cannot cause incorporation of 5-fluorocytosine into DNA and has no direct effect on DNA (cytosine-5)-methyltransferase.

Several intracellular targets of the present disclosure were identified as essential enzymes required for the biosynthesis and function of DNA. These enzymes are susceptible for inhibition by a multitude of cellular metabolites of the present disclosure, contributing to the observed cytotoxicity. The intracellular metabolites responsible for enzyme inhibitory activity are all phosphorylated derivatives and were found to be the following: 2',2',5-trifluorodeoxycytidine monophosphate, $F_3dCMP$, inhibitor of deoxycytidylate deaminase (DCTD); 2',2',5-trifluorodeoxyuridine monophosphate, $F_3dUMP$, inhibitor of thymidylate synthase (TS); 2',2',5-trifluorodeoxycytidine diphosphate, $F_3dCDP$ inhibitor of ribonucleotide reductase (RR); 2',2',5-trifluorodeoxycytidine triphosphate, $F_3dCTP$, inhibitor of DNA polymerase alpha (Pol α); 2',2',5-trifluorodeoxyuridine triphosphate, $F_3dUTP$, inhibitor of DNA polymerase alpha (Pol α), 5-fluorocytosine, FC incorporated into DNA, inhibitor of DNA (cytosine-5)-methyltransferase (MTase). These are summarized in Table 1.

TABLE 1

Multiple enzyme targets.

| Targets | Inhibitory metabolites | Reversibility |
|---|---|---|
| DCTD (minor) | $F_3$dCMP | reversible |
| TS (major) | $F_3$dUMP | Irreversible* |
| RR (major) | $F_3$dCDP | Irreversible* |
| Pol α (major) | $F_3$dCTP, $F_3$dUTP | Irreversible** |
| MTase (major) | 5-FC in DNA | Irreversible* |

*Inactivation by covalent bond formation at the active site;
**inhibition by DNA chain termination and/or DNA fragmentation.

It is one of the unique aspects of the present disclosure that inhibitory activities by the nucleotide metabolites of compounds of Formula I are observed at all levels of phosphorylation: monophosphate ($F_3$dCMP), diphosphate ($F_3$dCDP), triphosphate ($F_3$dCTP, $F_3$dUTP) and polynucleotide (5-FC-containing DNA).

The inhibition of the enzyme targets, TS, RR, and MTase is irreversible, due to mechanism-based inactivation caused by the inhibitory metabolites. The molecular mechanism of the inactivation involves covalent bond formation with the sulfhydryl groups of the active site cysteine residues essential for enzyme activity (see Examples 6, 7 and 8).

The observed misincorporation into nucleic acids may contribute to the biological activity of the disclosed compounds. Misincorporation into DNA of uracil in place of thymine, as a consequence of the inhibition of thymidylate synthase (TS), leads to DNA fragmentation resulting in cell death. Misincorporation of $F_3$dCMP and $F_3$dUP into DNA in place of dC and dT, respectively, lead to DNA damage. In addition, misincorporation of $F_3$dCMP into DNA in place of dC leads to inactivation of DNA (cytosine-5)-methyltransferase (MTase), resulting in DNA demethylation, disrupting epigenetic regulation of cellular metabolism. This represents an unexpected effect of the fluoropyrimidines of the present disclosure because no such effect was observed in any of the prior fluoropyrimidines in their six decades of therapeutic use.

The misincorporation into RNA by the conventional fluoropyrimidines, while could be a contributing factor to their cytotoxicity, affects non-dividing cells in normal tissues as well, thereby lowering the therapeutic index of these drugs.

Tested against the National Cancer Institute's panel of human cell lines in culture, the disclosed compounds were found to have a broad spectrum of significant growth inhibitory activities. A sample of the variety of human cancer cell lines, whose growth was inhibited more than 50% by 10 micromolar concentration of the prototype drug 6a, is shown in Table 2.

TABLE 2

Growth inhibitory activities against human cancer cell lines.

| Cell line | % Growth Inhibition* |
|---|---|
| ACHN | 86.4 |
| HL60 | 75.8 |
| NCI-H522 | 61.1 |
| HCT-116 | 63.5 |
| M14 | 85.9 |
| MCF-7 | 51.9 |
| OVCAR-8 | 71.6 |

*by 10 micromolar 6a

The description of the human cancer cell lines used is as follows: ACHN, human renal adenocarcinoma; HL-60(TB), human acute myeloid leukemia; HCT-116, human colon carcinoma; HOP-62, human adenocarcinoma (non-small cell lung cancer); M14, human metastatic malignant melanoma; MCF7, human mammary adenocarcinoma; OVCAR-8, human ovarian carcinoma.

These results demonstrate that the present disclosure show inhibitory activities against cancer derived from different tissues (leukemias, as well as solid tumors).

Using the cell viability assay of Promega, the following $IC_{50}$-values were obtained against KG-1 human acute myeloid leukemia cells (Table 3). The nucleoside carbamate capecitabine (Xeloda®) is included for comparison).

TABLE 3

Cell Viability Data.

| Compound | $IC_{50}$, μM | Ratio* |
|---|---|---|
| 6a | 0.129 ± 0.0107 | 69 |
| 5 | 0.0341 ± 0.00527 | 253 |
| Capecitabine | 8.92 ± 1.54 | 1 |

*$IC_{50}$—value of capecitabine/$IC_{50}$—value of test compound

The prototype Formula I compound 6a, with the pentyloxycarbonyl side chain showed a 69-fold higher potency, than capecitabine with the same side chain. Compound 5, the major intracellular nucleoside metabolite of Formula I compounds ($F_3$dCyd, see FIG. 2) showed a 253-fold higher potency than capecitabine.

The present disclosure provides compositions comprising one or more compounds of Formula I. The compositions can comprise one or more pharmaceutically acceptable carriers.

Compositions comprising one or more compounds of the disclosure and a pharmaceutical carrier can be prepared at a patient's bedside, or by a pharmaceutical manufacturer. In either case, the compositions or their ingredient can be provided in any suitable container, such as a sealed sterile vial or ampoule, and may be further packaged to include instruction documents for use by a pharmacist, physician or other health care provider. The compositions can be provided in combination with any suitable delivery form or vehicle, examples of which include liquids, caplets, capsules, tablets, inhalants or aerosol, etc. The delivery devices may comprise components that facilitate release of the pharmaceutical agents over certain time periods and/or intervals, and can include compositions that enhance delivery of the pharmaceuticals, such as nanoparticle, microsphere or liposome formulations, a variety of which are known in the art and are commercially available. In addition, procedures and special compositions are known in the art that enable delayed or sustained release of the active pharmaceutical ingredient. Further, each composition described herein can comprise one or more pharmaceutical agents.

The compositions described herein can include one or more standard pharmaceutically acceptable carriers. Pharmaceutically acceptable carriers are determined in part by the particular composition being administered, as well as by the particular method used to administer the composition. Accordingly, there are a wide variety of suitable formulations of pharmaceutical compositions of the present disclosure. Some examples of pharmaceutically acceptable carriers can be found in: *Remington: The Science and Practice of Pharmacy* (2005) 21st Edition, Philadelphia, Pa. Lippincott Williams & Wilkins. Effective formulations include oral and nasal formulations, formulations for parenteral administration, and compositions formulated for with extended release.

Examples of compositions, which may be suitable for oral administration, include, but are not limited to, (a) liquid solutions, such as an effective amount of a compound of the present disclosure suspended in diluents, such as water, saline or PEG 400; (b) capsules, sachets, depots or tablets, each containing a predetermined amount of the active ingredient, as liquids, solids, granules or gelatin; (c) suspensions in an appropriate liquid; (d) suitable emulsions; and (e) patches. The liquid solutions described above can be sterile solutions. The compositions can comprise, for example, one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers.

A composition can be in unit dosage form. In such form the composition is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. The compositions can deliver the compounds of the disclosure in a sustained release formulation.

The present disclosure provides methods of using one or more compounds of the present disclosure. For example, the compounds can be used to treat cancer and/or viral infections.

The steps of the method described in the various embodiments and examples disclosed herein are sufficient to carry out the methods of the present invention. Thus, in an embodiment, the method consists essentially of a combination of the steps of the methods disclosed herein. In another embodiment, the method consists of such steps.

For example, a method of treating comprises administering to an individual one or more compound of the present disclosure or a composition comprising one or more compounds of the present disclosure.

The method can be carried out in an individual who has been diagnosed with or is suspected of having cancer or a viral infection (i.e., therapeutic use). A method can also be carried out in individuals who have a relapse or a high risk of relapse after being treated for cancer or a viral infection.

For example, a method of the present disclosure can be carried out such that upon exposing a compound or composition of the present disclosure to a cancer cell causes analog misincorporation into DNA, resulting in alteration of the structure and function of DNA that may lead to the death of the cancer cell.

For example, a method of the present disclosure can be carried out such that ribonucleotide reductase, DNA polymerase α, thymidylate synthase, DNA (cytosine-5)-methyltransferase, or a combination thereof are inhibited using compounds of the present disclosure.

Various cancers may be treated with a compound or method of the present disclosure. Examples of cancers include, but are not limited to, renal adenocarcinoma, myeloid leukemia, colon carcinoma, non-small cell lung cancer, metastatic malignant melanoma, mammary adenocarcinoma, pancreatic adenocarcinoma, ovarian carcinoma, and the like, and combinations thereof.

A method of the present disclosure can be carried out in an individual in need of prophylaxis or treatment for viral infections/illnesses. Viral targets include, but are not limited to, HIV, HBV, HCV, HSV1 and HSV2. For example, a method of treating a viral infection comprises administering to an individual in need of treatment a compound or composition of the present disclosure, such that the virus is eliminated or the individual is cured from the virus.

Compositions comprising the compounds described herein can be administered to an individual using any known method and route, including oral, parenteral, subcutaneous, intraperitoneal, intrapulmonary, intranasal, and intracranial injections. Parenteral infusions include intramuscular, intravenous, intraarterial, intraperitoneal, and subcutaneous administration. Administration also includes topical and/or transdermal administrations.

The dose of the composition comprising a compound of the disclosure and a pharmaceutical agent will necessarily be dependent upon the needs of the individual to whom the composition of the disclosure is to be administered. These factors include, for example, the weight, age, sex, medical history, and nature and stage of the disease for which a therapeutic or prophylactic effect is desired. The compositions can be used in conjunction with any other conventional treatment modality designed to improve the disorder for which a desired therapeutic or prophylactic effect is intended, non-limiting examples of which include surgical interventions, radiation therapies, and immunotherapy. For example, the compositions are used in combination with (e.g., co-administered with) one or more known anti-cancer drug (e.g., DNA damaging anticancer drugs) or known antiviral drug. For example, compositions of the present disclosure can be administered with other anticancer drugs (e.g., anticancer drugs other than a compound of the present disclosure) such as, for example, leucovorin, docetaxel, irinotecan, oxaliplatin, and the like, and combinations thereof.

Methods of the present disclosure can be used on various individuals. In various examples, an individual is a human or non-human mammal. Examples of non-human mammals include, but are not limited to, farm animals, such as, for example, cows, hogs, sheep, and the like, as well as pet or sport animals such as horses, dogs, cats, and the like. Additional non-limiting examples of individuals include rabbits, rats, mice, and the like. The compounds or compositions of the present disclosure can be administered to individuals for example, in pharmaceutically-acceptable carriers, which facilitate transporting the compounds from one organ or portion of the body to another organ or portion of the body.

The following examples are presented to illustrate the present disclosure. They are not intended to be limiting in any manner.

Example 1

This example provides a description of the synthesis of 3',5'-Di-O-benzoyl-2'-deoxy-2',2',5-trifluorocytidine (4).

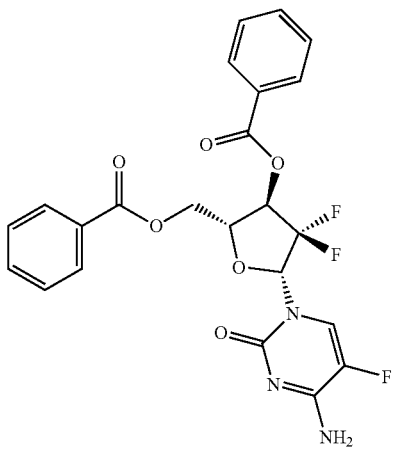

3',5'-Di-O-benzoyl-2'-deoxy-2',2',5-trifluorocytidine

5-Fluorocytosine (1, 23.1 g, 178.9 mmol) was treated with hexamethyldisilazane (HMDS, 1,000 mL) in the presence of ammonium sulfate ($NH_4SO_4$, 679 mg) under argon and refluxed at 125° C. for 5 hours. The volatiles were removed in vacuo under argon atmosphere to obtain 2 as a white solid. It was dissolved in dry dichloroethane (400 mL) and a solution of 3,5-di-O-benzoyl-2-deoxy-2,2-difluoro-1-O-mathanesulfonyl-α-D-ribofuranoside (3, 32 g, 70.16 mmol), in dry dichloroethane (300 mL) was added to it. The reaction mixture was stirred at room temperature for 10 minutes (min). TMSOTf (38 mL, 210.5 mmol was then added and the mixture was stirred at 95° C. for 16 hours (hrs) under argon. The reaction mixture was cooled to room temperature and then a saturated solution of $NaHCO_3$ was added, followed by stirring for 10 min. The resulting phases were separated and the aqueous phase was extracted with dichloromethane. The organic phases were treated with $NaHCO_3$ and brine, dried with $MgSO_4$ and concentrated in vacuo to give 4 as a pale yellow solid (37 g). NMR and LCMS analysis established that compound 4 was obtained as a 1.2:1.0 mixture of a and 3 anomers. Compound 4 was used to the next step without further purification.

Example 2

This example provides a description of the synthesis of 2'-Deoxy-2',2',5-trifluorocytidine (5).

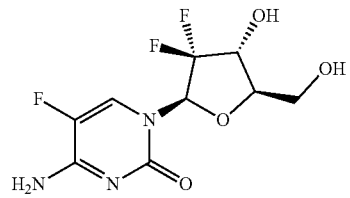

2'-Deoxy-2',2',5-trifluorocytidine

Compound 4 (see Example 1, 33.9 g, 69.3 mmol) was stirred at room temperature with 7N $NH_4OH$ in MeOH (190 mL) overnight. The volatiles were evaporated and the residue was partitioned between $CH_2Cl_2$ and $H_2O$. The aqueous phase was extracted with $CH_2Cl_2$ (3×) then evaporated to dryness. The residue was slurried in i-PrOH (75 mL) and warmed to 60° C., then conc. HCl was added in one portion (15 mL). the thick suspension was cooled to room temperature and white crystals formed immediately, which were filtered off and washed with cold i-PrOH, petroleum ether and $Et_2O$ to give compound 5 as 1.5:1.0 mixture of the α/β anomers. The latter was suspended in $H_2O$ at 60° C., and then 4N NaOH was added slowly to bring the mixture into solution, then the pH was adjusted to ~8.3 with 1N NaOH. A solid precipitated out, which was collected and washed with ice-cold water, dried in vacuo to yield the free amine 5 as a white solid (5.85 g) with a 30% yield over 3 steps (100% of the β-anomer by HPLC): mp 118-121° C.; $[\alpha]_D$=+79.640 (c 0.28, MeOH). LCMS (C-18, 5% isocratic $H_2O$/MeCN): ELSD (peak 1.065 min), UV (peak 0.96 min), positive mode: m/z=282 [M+H]+; negative mode: m/z=280 [M−H]−, 316 [M+Cl]−. $C_9H_{10}F_3N_3O_4$ (281.19).

$^1$H NMR (DMSO-$d_6$) δ=3.79 (dd, 1H, H-5'), 3.80 (m, 2H, H-4', H-5"), 4.18 (m, 1H, H-3'), 5.34 (br t, 1H, 5'-OH), 6.05 (t, $J_{1',F}$=7.35 Hz, 1H, H-1'), 6.25 (br d, 1H, 3'-OH), 7.75, 8.00 (2s, 2H, $NH_2$), 8.04 (d, $J_{6,F}$=7.23 Hz, 1H, H-6).

H,H-NOESY: 4.18 (H-3') correlates with 8.04 (H-6); 6.05 (H-1') correlates with 3.8 (H-4').

$^1$H HNR ($D_2O$): δ=3.88 (dd, 1H, $J_{gem}$=13.23 Hz, $J_{5',4'}$=3.66 Hz, H-5'), 4.03 (dd, $J_{gem}$=12.99 Hz, H-5"), 4.08 (m, 1H, H-4'), 4.35 (m, 1H, H-3'), 6.19 (t, $J_{1',F}$=7.29 Hz, 1H, H-1'), 7.93 (d, $J_{6,F}$=6.36 Hz, 1H, H-6).

$^{13}$C NMR (DMSO-$d_6$) δ=58.67 (s, 1C, C-5'), 68.11 (t, $J_{3',F}$=22.23 Hz, 1C, C-3'), 80.44 (s, 1C, C-4'), 83.60 (t, $J_{1',F}$=31.51 Hz, 1C, C-1'), 122.98 (t, $J_{2',F}$=258.06 Hz, 1C, C-2'), 124.82 (d, $J_{6,F}$=32.18 Hz, 1C, C-6), 136.20 (d, $J_{5,F}$=242.39 Hz, 1C, C-5), 152.88 (s, 1C, C-2), 157.62 (d, $J_{4,F}$=13.77 Hz, 1C, C-4).

Example 3

This example provides a description of the synthesis of 2'-Deoxy-2',2',5-trifluorocytidine hydrochloride (5.HCl).

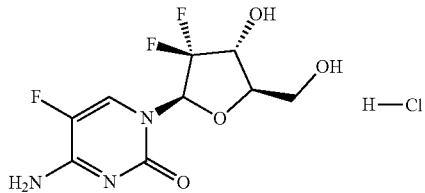

2'-Deoxy-2',2',5-trifluorocytidine hydrochloride

To a suspension of compound 5 (see Example 2, 5.85 g, 20.8 mmol) was added conc. HCl (5 mL) at 60° C. Upon cooling to room temperature, crystallization occurred. The crystals were filtered, washed with i-PrOH, petroleum ether and $Et_2O$, then dried in vacuo to give 5.HCl as a white solid (5.85 g, 89% from 5): mp 128-135° C.; $[\alpha]_D$=+52.23° (c 0.28, MeOH). LCMS (C-18; 5% isocratic $H_2O$/MeCN): ELSD (peak at 1.08 min), UV (peak at 0.975 min), positive mode: m/z=282 [M+H]+; negative mode: m/z=280 [M−H]−, 316 [M+Cl]−. $C_9H_{11}F_3N_3O_4Cl$ (317.20).

$^1$H NMR (DMSO-$d_6$) δ=3.63 (dd, 1H, H-5'), 3.79 (m, 2H, H-4', H-5"), 4.18 (m, 1H, H-3'), 5.34 (t, $J_{OH,5'}$=5.16 Hz, 1H,

5'-OH), 6.06 (t, $J_{1',F}$=7.05 Hz, 1H, H-1'), 6.25 (br, 1H, 3'-OH), 7.75, 8.01 (2s, 2H, $NH_2$), 8.04 (d, $J_{6,F}$=7.17 Hz, 1H, H-6).

$^1$H HNR ($D_2O$): δ=3.88 (dd, 1H, $J_{gem}$=13.17 Hz, $J_{5',4'}$=3.6 Hz, H-5'), 4.04 (dd, $J_{gem}$=13.59 Hz, H-5''), 4.09 (m, 1H, H-4'), 4.35 (m, 1H, H-3'), 6.20 (t, $J_{1',F}$=6.78 Hz, 1H, H-1'), 7.94 (d, $J_{6,F}$=6.24 Hz, 1H, H-6).

$^{13}$C NMR (DMSO-$d_6$) δ=58.68 (s, 1C, C-5'), 68.13 (t, $J_{3',F}$=22.57 Hz, 1C, C-3'), 80.51 (s, 1C, C-4'), 83.61 (t, $J_{1',F}$=32.84 Hz, 1C, C-1'), 122.99 (t, $J_{2',F}$=258.1 Hz, 1C, C-2'), 124.80 (d, $J_{6,F}$=32.63 Hz, 1C, C-6), 136.22 (d, $J_{5,F}$=242.42 Hz, 1C, C-5), 152.94 (s, 1C, C-2), 157.67 (d, $J_{4,F}$=13.75 Hz, 1C, C-4).

Example 4

This example provides a description of the synthesis of $N^4$-Pentyloxycarbonyl-2'-deoxy-2',2',5-trifluorocytidine (6a) ((pentyl (1-((2R,4R,5R)-3,3-difluoro-4-hydroxy-5-(hydroxymethyl)tetrahydrofuran-2-yl)-5-fluoro-2-oxo-1,2-dihydropyrimidin-4-yl)carbamate)).

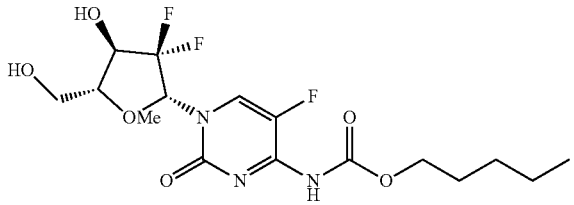

N4-Pentyloxycarbonyl-2'-deoxy-2',2',5-trifluorocytidine

A solution of trifluoronucleoside 5 (1.0 g, 3.5 mmol) in acetonitrile (30 mL) and pyridine (2 equiv) was cooled to 4° C. and to it was added HMDS (1.1 equiv). A solution of amyl chloroformate (1.0 equiv) in dichloromethane was then added dropwise maintaining the solution at 4° C. The mixture was then warmed to room temperature and stirred an additional 2 hours. Water (30 mL) was added and the organics extracted with dichloromethane (2×30 mL), dried with $MgSO_4$ and concentrated in vacuo. The crude product 6a (1.4 g) so obtained was shown to be a mixture of 6a and the 5'-carbonate. To a solution of the crude product (1.4 g) in MeOH (30 mL) was added sodium methoxide (0.6 mL, 25 wt % in MeOH) and the reaction mixture was allowed to stir at room temperature for 2.5 hours. The reaction mixture was then brought to pH 7 with Amberlite $H^+$ resin. The mixture was then filtered and concentrated in vacuo. Purification by flash chromatography (0-10% MeOH in EtOAc) yielded 6a as a white solid (0.89 g, 66% yield): mp 75-86° C.; m/z=396 [M+H]+; HPLC (UV, 260 nm) 99.46%.

$^1$H NMR (DMSO-$d_6$): δ=0.86-0.91 (m, 3H, $CH_3$), 1.31-1.33 (m, 4H, $CH_2$), 1.59-1.63 (m, 2H, $CH_2$), 3.62-3.67 (m, 1H, H-5'), 3.84-3.90 (m, 2H, H-4', H-5'), 4.08-4.20 (m, 2H, $CH_2$), 4.24-4.67 (m, 1H, H-3'), 5.42 (m, 1H, OH), 6.06 (m, 1H, H-1'), 6.34 (d, $J_{6,F}$=6.3 Hz, 1H, H-6), 8.40 (br s, 1H, OH), 10.66 (br s, 1H, NH).

$^{13}$C NMR (DMSO-$d_6$) δ=14.9 (s, 1C, $CH_3$), 21.2 (s, 1C, $CH_2$), 28.6 (d, 1C, $CH_2$), 58.6 (s, 1C, C-5'), 65.1 (s, 1C, $CH_2$), 67.4 (t, 1C, C-3'), 80.2 (s, 1C, C-4'), 84.1 (t, 1C, C-1'), 119.7 (s, 1C, C-2'), 122.3 (s, 1C, C-6), 125.5 (s, 1C, C-5).

HSQC ($D_2O$): 7.85 ppm (H-6) correlates with 130 ppm (C-6).

$^{19}$F NMR (DMSO-$d_6$): δ=−159 (s, 1F, F-5), −117 (s, 2F, F-2').

Example 5

This example provides a description of structure-activity relationships.

The structural determinants required for the pharmacological activities of compounds of Formula I have been established. The characteristic molecular features of Formula I are encircled:

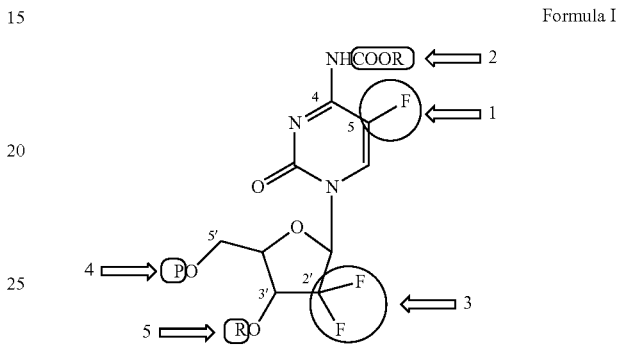

Formula I

Moiety 1: fluorine at the 5-position of the pyrimidine ring is essential for inhibition of both thymidylate synthase (TS) and DNA (cytosine-5)-methyl transferase;

Moiety 2: is a prodrug modifying substituent on the $N^4$-position of the 5-fluorocytosine base, which directs the compounds of Formula I primarily to the liver for metabolic activation by hepatic carboxyl esterases CES1 and CES2, thereby lessening gastro-intestinal toxicity, a characteristic toxic side effect of the fluoropyrimidines;

Moiety 3: the geminal difluoro substituents at the 2'-position of the 2'-deoxyribose sugar is essential for inhibition of ribonucleotide reductase and DNA polymerase c and is responsible for resisting cleavage by thymidine phosphorylase to form 5-fluorouracil;

Moiety 4: is a prodrug modifying substituent on the 5'-OH group of the 2',2'-difluoro-2'-deoxyribose sugar that may enable the delivery of the intact 5'-monophosphate forms of compounds of Formula I into cells; when P is a triphosphate, the corresponding metabolite can serve as a substrate for DNA polymerase and can cause misincorporation into DNA;

Moiety 5: is a hydrolysable 3'-OH-protecting group that modulates solubility and permeability properties; it is removed during metabolism by enzyme-catalyzed hydrolysis.

Example 6

This example provides an illustration for the molecular mechanism of the inactivation of thymidylate synthase (TS) by the $F_3$dUMP metabolite.

$F_3$dUMP acts as a suicide substrate of the enzyme thymidylate synthase by forming a covalent ternary complex with the enzyme and the cofactor 5,10-methylenetetrahydrofolate. The binding of the inhibitor to the enzyme is by a covalent bond to the SH-group of the active site cysteine residue involved in catalysis:

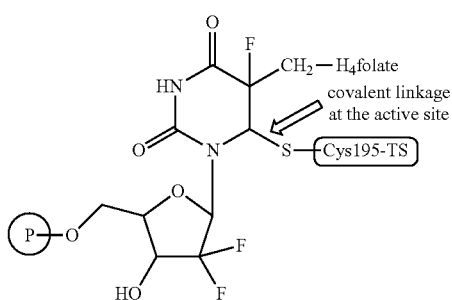

Example 7

This example provides an illustration for the molecular mechanism of the inactivation of ribonucleotide reductase (RR) by the $F_3dCDP$ metabolite.

$F_3dCDP$ acts as a suicide substrate of the enzyme forming a binary complex between the inhibitor and the enzyme via a covalent bond to the SH-group of the active site cysteine residue:

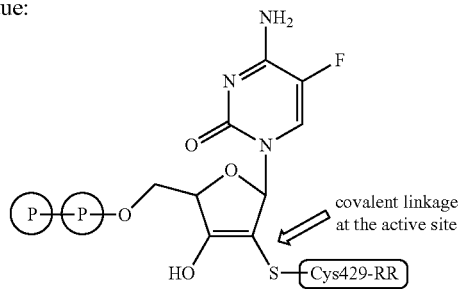

Example 8

This example provides an illustration for the molecular mechanism of the inactivation of DNA (cytosine-5)-methyltransferase (MTase) by the $F_3dCMP$ metabolite incorporated into DNA.

The 5-fluorocytosine moiety of the misincorporated $F_3dCMP$ into DNA acts as a suicide substrate of the enzyme DNA (cytosine-5)-methyltransferase (MTase) by forming a covalent binary complex with the enzyme and becoming methylated in the process. The binding to the enzyme is by a covalent bond to the SH-group of the active site cysteine residue involved in catalysis. The mechanism of enzyme inactivation is analogous to that described for TS in Example 6.

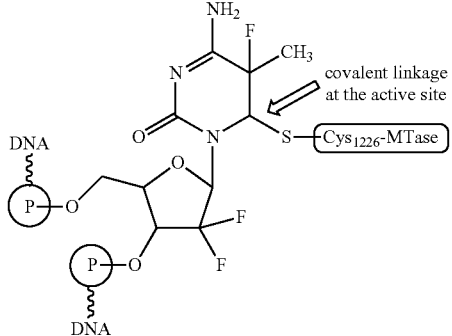

Example 9

This example provides a description of a mechanism of the metabolic activation of the $N^4$-alkylcarbamate prodrug moiety.

Enzymatic hydrolysis catalyzed by hepatic carboxyl esterases CES1 and CES2 liberates the free amino group at the 4-position of the pyrimidine ring:

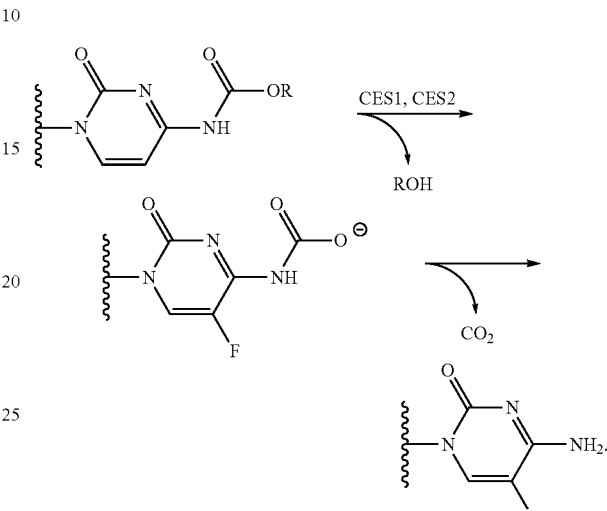

Example 10

This example provides a description of mechanism of the metabolic activation of the amino acid ester phosphorodiamidate prodrug ("pronucleotide") moiety at the 5'-position of the 2',2'-difluoro-2'-deoxyribose moiety.

Intracellular esterase hydrolysis of the 5'-substituent of Formula I (R"=phosphorodiamidate), followed by cyclization leads to a cyclic phosphoester intermediate that collapses into a monophosphoramidate. Further hydrolysis by the phosphoramidase activity of HINT1 results in the formation of $F_3dCMP$, the first intracellular phosphorylated metabolite of compounds of Formula I that serves as a substrate and competitive inhibitor of the enzyme dCMP deaminase, and is a precursor of all the other inhibitory nucleotides described above (see Table 1).

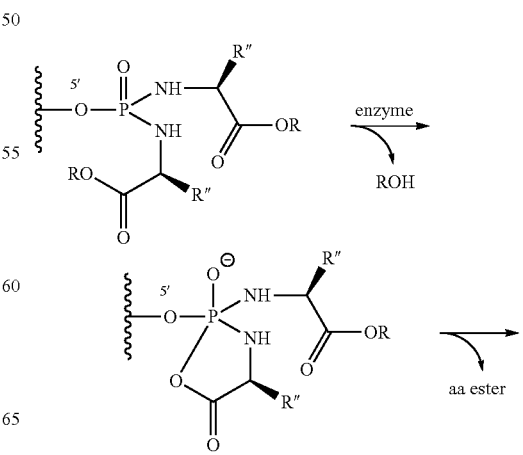

-continued

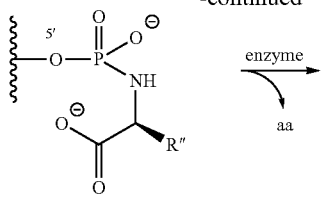

F₃dCMP

Example 11

This example provides a description of HCT-116 xenograft test for in vivo oral anticancer activity of 6a.

Forty athymic nude mice (NCr nude, female, 5-6 weeks old, 20-25 g, Taconic) were inoculated with $6\times10^6$ exponentially growing human colon cancer HCT-116 cells, 1:1 ratio with Matrigel in 100 microliter into the right flank. Over the following 10 days, tumors reached a volume of 70 to 130 mm³. Tumor volume were caliper-measured and calculated as length×width×width/2. Thirty mice were randomly allocated into three groups: (1) vehicle control group, (2) 6a test group, and (3) capecitabine (Cayman Chemical Co.) positive control group, with 10 mice into each group. Dosing solutions of each were prepared and kept refrigerated during the course of the test. Each mouse was dosed daily by oral administration.

After starting the dosing, body weights and tumor size measurements were recorded twice weekly to the end of the test.

Figure 3:
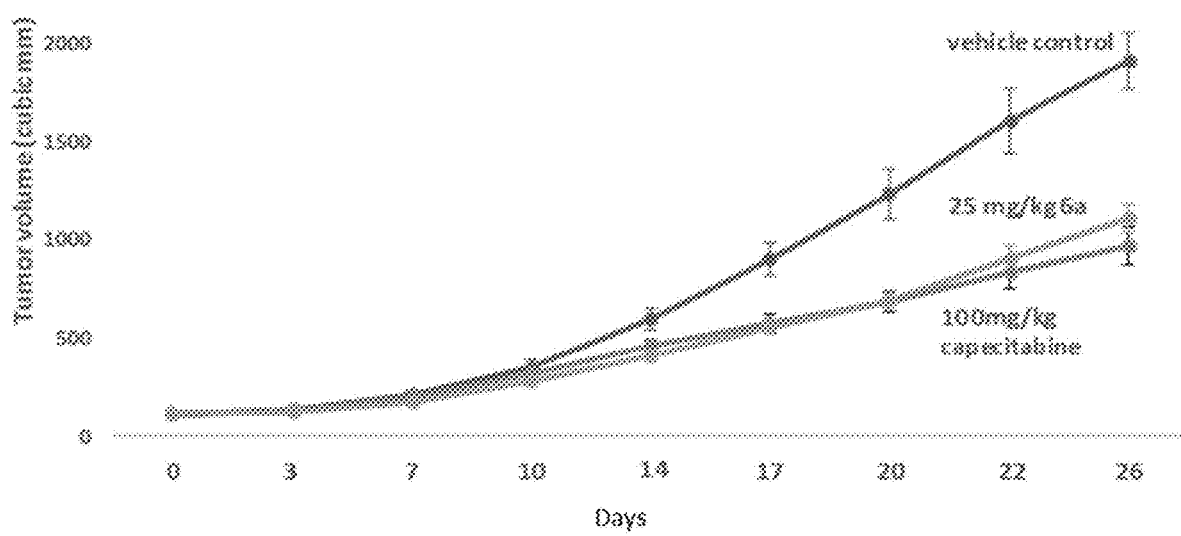
FIG. 3 shows in vivo oral efficacy of 6a, in comparison with that of capecitabine.

These results are graphically illustrated (see FIG. 3), demonstrating that 6a, a representative of the Formula I compounds, is orally active in vivo, by inhibiting the growth of human colon cancer in mice, superior to capecitabine, the most advanced, clinically used anticancer fluoropyrimidine with oral bioavailability. The results show that about 4-times higher dose of capecitabine (100 mg/kg) was required to achieve comparable anticancer activity to that of 6a (25 mg/kg).

Although the present disclosure has been described with respect to one or more particular embodiments and/or examples, it will be understood that other embodiments and/or examples of the present disclosure may be made without departing from the scope of the present disclosure.

The invention claimed is:

1. A compound having the following structure:

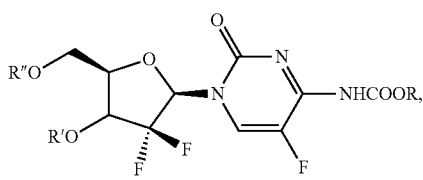

wherein R is selected from the group consisting of $C_1$ to $C_7$ linear alkyl groups and $C_1$ to $C_7$ branched alkyl groups; R' is selected from the group consisting of H and a hydroxy protecting groups; R" is selected from the group consisting of H, a phosphate ester, an amino acid $C_1$ to $C_7$ alkyl ester phosphoramidate, and a phosphorodiamidate or a pharmaceutically acceptable salt thereof.

2. The compound of claim 1, wherein the hydroxy protecting group is selected from the group consisting of acetyl and benzoyl.

3. The compound of claim 1, wherein the R" is a monophosphate, diphosphate, triphosphate, or phosphoramidate.

4. The compound of claim 1, wherein the compound has the following structure:

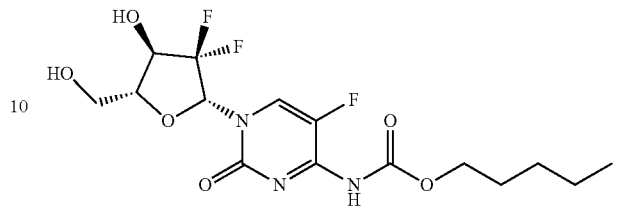

(pentyl (1-((2R,4R,5R)-3,3-difluoro-4-hydroxy-5-(hydroxymethyl)tetrahydrofuran-2-yl)-5-fluoro-2-oxo-1,2-dihydropyrimidin-4-yl)carbamate).

5. A composition comprising a compound of claim 1 and a pharmaceutically acceptable carrier.

6. The composition of claim 5, wherein the composition further comprises one or more anticancer drugs.

7. The composition of claim 6, wherein the one or more anticancer drugs is chosen from leucovorin, docetaxel, irinotecan, oxaliplatin, and combinations thereof.

8. The composition of claim 5, wherein the compound is:

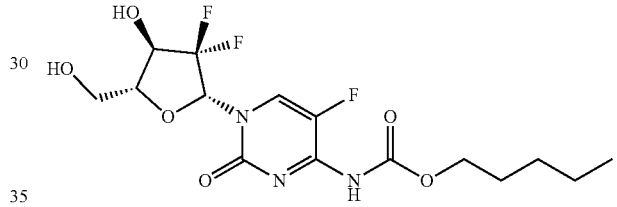

(pentyl (1-((2R,4R,5R)-3,3-difluoro-4-hydroxy-5-(hydroxymethyl)tetrahydrofuran-2-yl)-5-fluoro-2-oxo-1,2-dihydropyrimidin-4-yl)carbamate).

9. The composition of claim 8, wherein the composition further comprises one or more anticancer drugs.

10. The composition of claim 9, wherein the one or more anticancer drugs is chosen from leucovorin, docetaxel, irinotecan, oxaliplatin, and combinations thereof.

11. A method for treating an individual having cancer comprising administering to the individual a composition of claim 5, wherein administering the composition results in inhibition of cancer growth in the individual.

12. The method of claim 11, wherein the individual is a human or non-human mammal.

13. The method of claim 11, wherein the cancer is selected from the group consisting of renal adenocarcinoma, myeloid leukemia, colon carcinoma, non-small cell lung cancer, metastatic malignant melanoma, mammary adenocarcinoma, pancreatic adenocarcinoma, and ovarian carcinoma.

14. The method of claim 13, wherein the cancer is colon carcinoma.

15. The method of claim 13, wherein the cancer is pancreatic adenocarcinoma.

16. The method of claim 13, wherein the cancer is mammary adenocarcinoma.

17. The method of claim 11, wherein DNA synthesis in a cancer cell in inhibited.

18. The method of claim 11, wherein ribonucleotide reductase, DNA polymerase α, thymidylate synthase, DNA (cytosine-5)-methyltransferase, or a combination thereof are inhibited.

19. The method of claim 11, wherein method induces analog misincorporation into DNA, resulting in alteration of the structure and function of DNA, leading to the death of a cancer cell.

20. The method of claim 11, wherein the composition comprises at least one compound having the following structure:

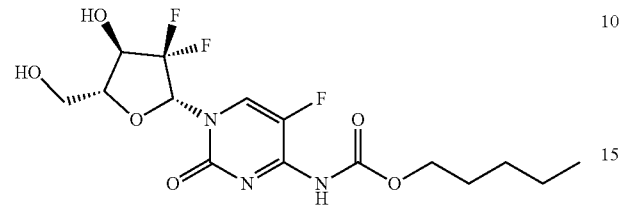

(pentyl (1-((2R,4R,5R)-3,3-difluoro-4-hydroxy-5-(hydroxymethyl)tetrahydrofuran-2-yl)-5-fluoro-2-oxo-1,2-dihydropyrimidin-4-yl)carbamate).

21. The method of claim 11, wherein the method further comprises radiotherapy, surgical intervention, and/or immunotherapy.

* * * * *